US00PP28990P2

(12) United States Plant Patent
Bédard

(10) Patent No.: US PP28,990 P2
(45) Date of Patent: Feb. 27, 2018

(54) GRANDIFLORA ROSE PLANT NAMED 'WEKMERORO'

(50) Latin Name: *Rosa hybrida*
Varietal Denomination: WEKmeroro

(71) Applicant: Early Morning LLC, Lawrenceburg, IN (US)

(72) Inventor: Christian Bédard, Placentia, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 15/530,255

(22) Filed: Dec. 15, 2016

(51) Int. Cl.
*A01H 5/02* (2006.01)

(52) U.S. Cl.
USPC ..... Plt./132

(58) Field of Classification Search
USPC ..... Plt./132
CPC ..... A01H 5/0222
See application file for complete search history.

(56) References Cited

U.S. PATENT DOCUMENTS

PP20,936 P2 4/2010 Carruth

OTHER PUBLICATIONS

Weeks Roses, 2017 Catalog, 92 pages.

*Primary Examiner* — Kent L Bell
(74) *Attorney, Agent, or Firm* — McKee, Voorhees & Sease, PLC

(57) ABSTRACT

A new variety of Grandiflora rose suitable for garden decoration, having flowers of fuchsia pink striped with bright white coloration.

1 Drawing Sheet

Classification: The present invention relates to a new *Rosa hybrida* plant.

Variety denomination: The new plant has the varietal denomination 'WEKmeroro'.

BACKGROUND OF THE INVENTION

This invention relates to a new and distinct variety of Grandiflora Rose. It has as its seed parent the variety known as 'WEKmeredoc' (not patented) and as its pollen parent the variety known as 'WEKgobnez' (U.S. Plant Pat. No. 20,936).

SUMMARY OF THE INVENTION

Among the features which distinguish the new variety from other presently available and commercial rose cultivars known to the inventor are the following combinations of characteristics: its strong citrus-like with hints of spices fragrance, its elegant flowers of fuchsia pink striped with bright white coloration, its excellent color stability throughout the life of the flowers and its abundant blooms. The plant has an upright bushy growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKmeroro' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKmeredoc' by the following combination of characteristics: whereas 'WEKmeroro' bears double flowers (about 23 to 40 petals) of fuchsia pink striped with bright white coloration, 'WEKmeredoc' bears double flowers of light pink with darker undertones coloration with significantly lesser petalage (about 17 to 25 petals). The new variety has an upright bushy medium height growing habit (about 135 to about 200 cm. in height), whereas the seed parent has a upright bushy significantly shorter growing habit (about 90 cm. in height).

The new variety may be distinguished from its pollen parent, 'WEKgobnez' by the following combination of characteristics: whereas 'WEKmeroro' bears double flowers (about 23 to 40 petals) of fuchsia pink striped with bright white coloration, 'WEKgobnez' bears double flowers of burgundy & cream striped bicolor coloration with significantly heavier petalage (about 41 to 66 petals). The new variety has an upright bushy medium height growing habit (about 135 to about 200 cm. in height), whereas the pollen parent has an upright moderately spreading shorter growing habit (about 140 to about 165 cm. in height).

COMPARISON WITH THE CLOSEST COMMERCIALLY AVAILABLE CULTIVAR

The closest commercially available cultivar to the new variety is the pollen parent 'WEKgobnez' (U.S. Plant Pat. No. 20,936).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of December.

Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of December. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in regular rounded clusters on strong short to medium length stems (about 22 to about 80 cm.). The cluster ranges from about 12.7 to about 18.3 cm. in diameter. Outdoors, the plant blooms abundantly and nearly continuously during the growing season. The flowers have a strong citrus-like with hints of spices fragrance.

BUD

The peduncle is about 2.4 to about 6.1 cm. in length, of average to somewhat heavy caliper (about 0.3 to about 0.4 cm. in diameter), and usually erect. It is mostly smooth, with few stipitate glands, and very few hairs. Peduncle color is between 146C and 146B often moderately suffused, especially on the side exposed to the sun, with between 187B and 183A.

Before the calyx breaks, the bud is about 1.2 to about 1.8 cm. in diameter at the widest point, about 1.8 to about 2.4 cm. in length, and pointed in shape. The surface of the bud bears between 6 to 11 foliaceous appendages with few stipitate glands and hairs, usually with slender entire foliaceous parts extending beyond the tip of the bud about ½ or more of its length. Bud color is between 137C and 146B often moderately suffused, especially on the side exposed to the sun, with between 187B and 187A.

The sepals are about 1.9 to about 3.7 cm. in length and about 0.8 to about 1.0 cm. in width at the widest point. The outer surface color of the sepal is between 137C and 146B often moderately suffused, especially on the side exposed to the sun, with between 187B and 187A. The outer surface of the sepal is moderately smooth and bears between 0 to 5 foliaceous appendages with few stipitate glands and hairs. The inner surface color of the sepal is near 146B broadly bordered by near 137C. After the sepals open, the inner surface color is sometimes lightly suffused, especially on the area exposed to the sun, with 187A and 187B. The inner surface of the sepal is covered with fine wooly tomentum; margins are lined with few stipitate glands and hairs.

The receptacle of the flower is of somewhat short length (about 0.4 to about 0.8 cm.) and moderately thin in caliper (about 0.5 to about 0.9 cm. in diameter). The receptacle is cup-shaped in form. Its surface is smooth with few hairs and with moderately thick fleshy walls. The receptacle color is between 144A and 146A.

As the petals open (after the calyx breaks), the bud is about 1.5 to about 2.4 cm. in diameter at the widest point, about 2.2 to about 2.9 cm. in length, and pointed to somewhat ovoid in form. The color of the under and upper surfaces of the newly opened petals is irregularly striped and flecked with as dark as between 60A and 57C to as light as between 155C and 155B. At the point where the petal attaches, there is a moderately small zone of between 150C and 1B.

BLOOM

When fully open, the bloom ranges from about 7.6 to about 11.2 cm. in diameter. Petalage is double with about 23 to 40 petals and about 4 to 12 petaloids irregularly arranged. When partially open, the bloom form is moderately high centered to cupped, and the petals are loosely spiraled to cupped with petal edges somewhat reflexed outward. When fully open, the bloom form is more cupped, and the petals are loosely cupped to somewhat undulated with petal edges moderately reflexed outward.

PETALS

The substance of the petals is moderately heavy and of somewhat thin to medium thickness, with upper surfaces slightly satiny and under surfaces moderately shiny. The petals are about 3.6 to about 5.7 cm. in length and about 3.1 to about 5.6 cm. in width at the widest point. Petal margins are entire.

The outer petals are moderately obovate to somewhat rounded in shape with rounded apices.

The inner petals are broadly obovate in shape with rounded apices.

Petaloids are about 0.6 to about 4.8 cm. in length and about 0.3 to about 3.6 cm. in width at the widest point. Petaloids are irregularly shaped somewhat oblanceolate to oblong with rounded apices.

NEWLY OPENED FLOWER

The under surface color of the outer, intermediate and inner petals is irregularly striped and flecked with as dark as between 64C and 61C to as light as between 155C and 155B. At the point where the petal attaches, there is a moderately small zone of between 155C and 155A. The upper surface color of the outer, intermediate and inner petals is irregularly striped and flecked with as dark as between 67B and 57C to as light as between 155C and 155B. At the point where the petal attaches, there is a moderately small zone of between 155C and 155A.

The under and upper surface colors of the petaloids are similar in coloration to the upper and under surfaces of the intermediate and inner petals.

The general tonality of the newly opened flower is irregularly striped and flecked with as dark as between 67B and 57C to as light as between 155C and 155B.

THREE-DAY-OLD FLOWER

The under surface color of the outer, intermediate and inner petals is irregularly striped and flecked with as dark as between 64C and 61C to as light as between 155C and 155B. At the point where the petal attaches, there is a moderately small zone of between 155C and 155A. The upper surface color of the outer, intermediate and inner petals is irregularly striped and flecked with as dark as between 67B and 57C to as light as between 155C and 155B. At the point where the petal attaches, there is a moderately small zone of between 155C and 155A.

The under and upper surface colors of the petaloids are similar in coloration to the upper and under surfaces of the intermediate and inner petals.

The general tonality of the three-day-old flower is irregularly striped and flecked with as dark as between 67B and 57C to as light as between 155C and 155B.

On the spent bloom, the petals usually drop off cleanly.

In December in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 135) and are arranged regularly about the pistils; a few are mixed with petaloids. The filaments are of somewhat short to medium length (about 0.4 to about 1.2 cm.) most with anthers. Filaments are between 1D and 154D in color sometimes lightly suffused with near 187D. The anthers are somewhat small for the class and all open approximately at the same time. Anther color when immature is near 20A on the external part and near 11D on the internal part. Anther color at maturity is near 165B on the external part and near 200A on the internal part. Pollen is moderate and between 22B and 23C in color.

FEMALE REPRODUCTIVE ORGANS

Pistils vary in number (average about 105). The styles are moderately even, average to somewhat long in length (about 0.7 to about 0.9 cm.), thin in caliper, and loosely bunched to somewhat separated. Stigma color is near 11C. Style color is between 154D and 1D often heavily suffused with between 53A and 53B. Ovaries are usually all enclosed in the calyx. The ovaries are of medium size and between 158B and 158C in color. Hips have not been observed on this variety when grown in Pomona, Calif.

FOLIAGE

The compound leaves are usually comprised of three to seven leaflets and are borne abundantly. The five-leaflet leaves are about 9.6 to about 16.1 cm. in length and about 8.7 to about 15.4 cm. in width at the widest point, moderately crisp to somewhat leathery in texture on both sides, and glossy in finish on the upper side and slightly glossy in finish on the underside. The leaves have a pinnate venation pattern. The terminal leaflets are about 4.4 to about 8.1 cm. in length and about 3.2 to about 6.8 cm. in width at the widest point, shaped ovate to somewhat oval with acute to somewhat acuminate apices and rounded to somewhat acute bases. Their margins are usually simply serrate.

The upper surface color of the mature leaf is between 139A and 147A. The under surface color of the mature leaf is between 137C and 146A. The under and upper colors of the leaf veins on the mature leaf are similar in coloration to the upper and under surfaces colors of the mature leaf. The upper surface color of the young leaf is between 137A and 146B, often heavily suffused with between 187A and 187B. The under surface color of the young leaf is near 146B, often heavily suffused with between 187B and 183A. The under and upper colors of the leaf veins on the young leaf are similar in coloration to the upper and under surfaces colors of the young leaf.

The rachis is somewhat light to average in caliper and rough. The upper side is deeply grooved with few hairs and stipitate glands on the edges of the grooves. The under side of the rachis is rough with few stipitate glands and small prickles. The rachis color is near 146C on the under side and near 137A on the upper side, often moderately suffused on the young leaves with between 187B and 183A.

The stipules are about 1.2 to about 2.5 cm. in length and moderately wide (about 0.5 to about 1.6 cm.) with long straight points that usually turn out at an angle of more than 45 degrees and sometimes recurve toward the stem. The under and upper surface color of the stipule is between 139A and 137A. The upper and under surfaces of the stipules are smooth in texture.

The petiole is somewhat light to average in caliper and rough. The upper side is deeply grooved with few hairs and stipitate glands on the edges of the grooves. The under side of the petiole is rough with few stipitate glands and small prickles. The petiole is about 0.8 to about 1.7 cm. in length and about 0.1 to about 0.2 cm in width at the widest point. The petiole color is near 146C on the under side and near 137A on the upper side, often moderately suffused on the young leaves with between 187B and 183A.

The plant displays an average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has an upright bushy medium height growing habit (about 135 to about 200 cm. in height and about 120 to about 140 cm. spread at the widest point), with full branching. It displays vigorous growth and the canes are of somewhat light to medium caliper for the class (about 1.2 to about 2.3 cm. in diameter at the widest point).

The color of the major stems is between 146A and 137C. The major stems are rough in texture and they bear many large prickles that are about 0.6 to about 1.2 cm. in length. The large prickles are angled slightly downward to somewhat hooked with a short somewhat broad oval base; prickle color is between 165A and 200D sometimes lightly suffused with between 201B and 201C. The major stem bears few small prickles of similar shape and coloration.

The color of the branches is between 146A and 147A. The branches are rough in texture and they bear some large prickles which are of similar size and shape to the large prickles on the major stems; prickle color is near 199A. The branches bear few small prickles of similar shape and coloration.

The color of the new shoots is between 146C and 144A often moderately suffused with between 187B and 183A. The new shoots are rough in texture and they bear some large prickles which are of similar size and shape to the large prickles on the major stems; prickle color is near 146B often moderately suffused with between 187B and 187C. The shoots bear few small prickles of similar shape and coloration.

I claim:

1. A new and distinct Grandiflora rose plant of the variety substantially as described and illustrated herein.

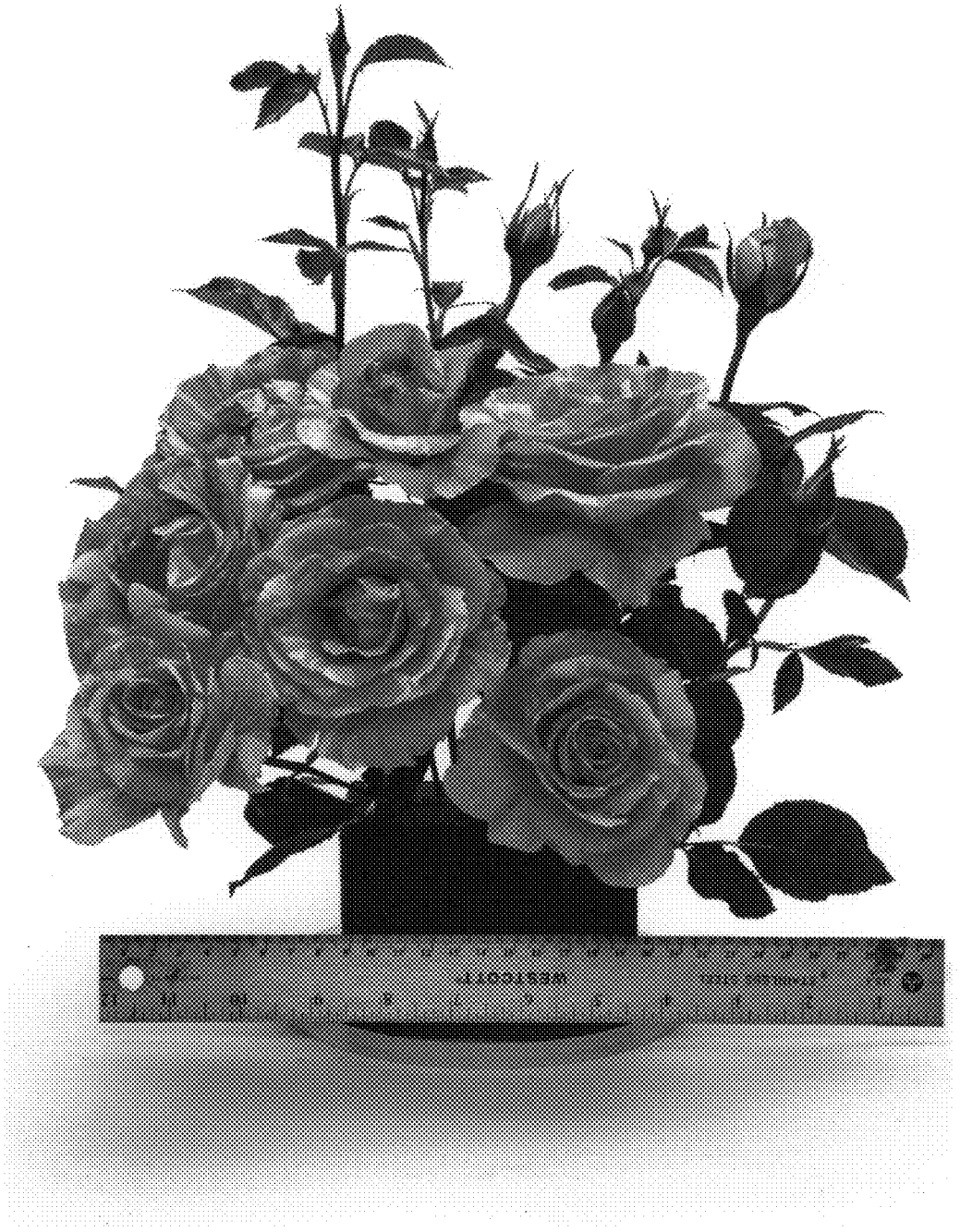

* * * * *